United States Patent
Abe et al.

(10) Patent No.: US 7,767,426 B2
(45) Date of Patent: Aug. 3, 2010

(54) METHOD OF PRODUCING RIBOFLAVIN

(75) Inventors: Kiyoshi Abe, Chuo-ku (JP); Hiroshi Nitta, Chuo-ku (JP); Enoch Y. Park, Shizuoka (JP); Hua Ming, Shizuoka (JP); Eun He Jung, Shizuoka (JP)

(73) Assignee: Mizusawa Industrial Chemicals, Ltd. (JP)

( * ) Notice: Subject to any disclaimer, the term of this patent is extended or adjusted under 35 U.S.C. 154(b) by 1187 days.

(21) Appl. No.: 10/503,617

(22) PCT Filed: Feb. 18, 2003
(Under 37 CFR 1.47)

(86) PCT No.: PCT/JP03/01730

§ 371 (c)(1),
(2), (4) Date: Aug. 5, 2004

(87) PCT Pub. No.: WO03/070962

PCT Pub. Date: Aug. 28, 2003

(65) Prior Publication Data

US 2005/0244919 A1    Nov. 3, 2005

(30) Foreign Application Priority Data

Feb. 19, 2002    (JP)    ............................. 2002-042168

(51) Int. Cl.
*C12P 17/18*    (2006.01)
*C12P 17/00*    (2006.01)
*C12P 17/16*    (2006.01)
*C12P 1/00*    (2006.01)

(52) U.S. Cl. ........................ 435/119; 435/41; 435/117; 435/118

(58) Field of Classification Search ......... 435/117–119, 435/41
See application file for complete search history.

(56) References Cited

U.S. PATENT DOCUMENTS 2,876,169 A * 3/1959 Malzahn et al. ............... 435/66

FOREIGN PATENT DOCUMENTS

| JP | A-36-8047   |   | 6/1936 |
| JP | A-04-122497 |   | 4/1992 |
| JP | 08-214875   | * | 8/1996 |
| JP | A-08-214875 |   | 8/1996 |

OTHER PUBLICATIONS www.answers.com, search "fuller's earth" http://www.answers.com/topic/fuller-s-earth, accessed Jun. 30, 2006.*
Reneae E. Coffman* and Dane O. Kildsig "Effect of Nicotinamide and Urea on the Solubility of Riboflavin in Various Solvents" Journal of Pharmaceutical Sciences / 951 vol. 85, No. 9, Sep. 1996.*

* cited by examiner

*Primary Examiner*—L Blaine Lankford
*Assistant Examiner*—Thane Underdahl
(74) *Attorney, Agent, or Firm*—H. Jay Spiegel; Robert L. Haines

(57) ABSTRACT

A method of producing riboflavin by culturing riboflavin-producing microbes in a culture medium using a plant oil or an animal oil as a carbon source, forming and accumulating riboflavin therein and collecting riboflavin therefrom, wherein a carrier of a clay mineral having oil-adsorbing property, a chemically treated product thereof or a calcium compound is made present in the culture medium. The riboflavin is produced maintaining a high yield and at an increased production rate at a low cost without requiring cumbersome operations for concentrating and recovering the riboflavin. It is further allowed to recover the riboflavin by effectively utilizing the waste plant oil or the waste animal oil that is to be disposed of.

1 Claim, 3 Drawing Sheets

METHOD OF PRODUCING RIBOFLAVIN

TECHNICAL FIELD

The present invention relates to a method of producing riboflavin. More particularly, the invention relates to a method of producing riboflavin from a carbon source of plant oils or animal oils in high yields and at high production rates by making present, in a culture medium for producing riboflavin, a carrier of a clay mineral having oil-adsorbing property, a chemically treated product thereof or a calcium compound.

BACKGROUND ART

There has long been known a method of producing riboflavin by culturing riboflavin-producing microbes in a culture medium, forming and accumulating riboflavin therein and collecting riboflavin therefrom. As the riboflavin-producing microbes, there have also been known to use *Eremothecium ashbyii, Ashbya gossypii, Candida flareri, Mycocandida riboflavina, Clostridium acetobutylicum*, as well as to use *Bacillus* riboflavin-producing microbes (Japanese Unexamined Patent Publication (Kokai) No. 66894/1974), variable strains of *Streptomyces testaceus* (Japanese Unexamined Patent Publication (Kokai) No. 116690/1975), Achromobactor riboflavin-producing microbes (Japanese Unexamined Patent Publication (Kokai) No. 54094/1977), *Previbacterium* riboflavin-producing microbes (Japanese Unexamined Patent Publication (Kokai) No. 110897/1977), *Saccharomyces* riboflavin-producing microbes (Japanese Unexamined Patent Publication (Kokai) No. 241895/1985), *Candida phamata* (ATCC 20849) (International Patent Publication No. 509221/1993).

As the carbon sources in the culture medium, there have further been known to use saccharides such as glucose and sucrose, starches or hydrolyzed products thereof, acetic acid, citric acid, ethanol, or hydrocarbons and benzoic acid for certain kinds of microorganisms.

However, when oils and fats are used as carbon sources, oils and fats must be dispersed in an aqueous culture medium. For this purpose, the culture medium must be stirred, or a dispersant or an emulsifier must be added into the system.

Under the stirring conditions where the oils are emulsified or suspended in water, however, it is confirmed that the microbes themselves are killed and destroyed resulting in a decrease in the yield of riboflavin.

According to the method of adding the dispersant or the emulsifier into the system, further, the microbes are inevitably and adversely affected by these drugs and, besides, the added drugs mixes into the riboflavin that is formed.

DISCLOSURE OF THE INVENTION

In studying a method of producing riboflavin by culturing the riboflavin-producing microbes in a culture medium using plant a oil or an animal oil as a carbon source, by forming and accumulating riboflavin therein and collecting riboflavin therefrom, the present inventors have discovered the fact that the riboflavin can be produced in high yields and at high production rates by stably dispersing the plant oil or the animal oil in the culture medium without the need of conducting the stirring to such an excess degree as to damage the microbes if a carrier of a clay mineral having oil-adsorbing property, a chemically treated product thereof or a calcium compound is made present in the culture medium.

In studying a method of producing the riboflavin by culturing the riboflavin-producing microbes in a culture medium using the plant oil or the animal oil as a carbon source, by forming and accumulating riboflavin therein and collecting riboflavin therefrom, further, the present inventors have discovered the fact that the waste plant oil or the waste animal oil that is to be disposed of can be effectively utilized by using a waste clay in which the carbon source is occluding the plant oil or the animal oil.

Namely, it is an object of the present invention to provide a method of producing riboflavin by culturing riboflavin-producing microbes in a culture medium using a plant oil or an animal oil as a carbon source, wherein the plant oil or the animal oil is dispersed in the culture medium in an improved manner, so that the riboflavin can be produced in high yields and at high production rates.

Another object of the present invention is to provide a method of producing riboflavin at a low cost without requiring cumbersome operations such as concentrating and recovering the riboflavin.

A further object of the present invention is to provide a method of recovering riboflavin by effectively utilizing the waste plant oil or the waste animal oil that is to be disposed of.

According to the present invention, there is provided a method of producing riboflavin by culturing riboflavin-producing microbes in a culture medium using a plant oil or an animal oil as a carbon source, forming and accumulating riboflavin therein and collecting riboflavin therefrom, wherein a carrier of a clay mineral having oil-adsorbing property, a chemically treated product thereof or a calcium compound is made present in the culture medium.

In the method of producing riboflavin of the present invention, it is desired that the carrier is made present in an amount of from 0.1 to 10% by weight in the culture medium.

According to a preferred embodiment of the present invention, it is desired that the carrier is a chained clay mineral and, particularly, that the carrier is a clay mineral having a fiber diameter of from 70 to 400 angstroms and a fiber length of from 0.2 to 400 μm.

According to another preferred embodiment of the present invention, it is desired that at least part of the carrier is a smectite clay mineral and an acid-treated product thereof.

As the carrier, further, there can be used a calcium compound which is desirably a calcium carbonate.

In the present invention, there is no particular limitation on the manner of making the carrier present in the culture medium. Depending upon the cases, however, it may be desired to make the carrier present in the culture medium in a state of occluding the plant oil or the animal oil, or to use the waste clay as the carrier occluding the plant oil or the animal oil.

According to the present invention, further, there is provided a method of producing riboflavin by culturing riboflavin-producing microbes in a culture medium using a plant oil or an animal oil as a carbon source, forming and accumulating riboflavin therein and collecting riboflavin therefrom, wherein the carbon source is the waste clay occluding the plant oil or the animal oil.

According to the present invention, further, there is provided a method of producing riboflavin by culturing riboflavin-producing microbes in a culture medium using a plant oil or an animal oil as a carbon source, forming and accumulating riboflavin therein and collecting riboflavin therefrom, wherein the carbon source is the oil component extracted from the waste clay occluding the plant oil or the animal oil.

BEST MODE FOR CARRYING OUT THE INVENTION

In the present invention, the riboflavin-producing microbes are culture medium using a plant oil or an animal oil as a carbon source, to form and accumulate riboflavin therein and to collect riboflavin therefrom. Here, a carrier of a clay mineral having oil-adsorbing property, a chemically treated product thereof or a calcium compound is made present in the culture medium. For example, a culture medium of which the pH has been adjusted containing a plant oil or an animal oil is sterilized and, then, riboflavin-producing microbes that have been cultured in advance are implanted and cultured. In this case, the above carrier is made present in the culture medium to promote the consumption of the plant oil or the animal oil thereby to improve the yield and production rate of riboflavin.

Basically, the present invention is based on a discovery that the yield of riboflavin is improved if a clay mineral having oil-adsorbing property, a chemically treated product thereof a calcium compound is made present in the culture medium at the time of culturing the riboflavin-producing microbes in the culture medium containing the plant oil or the animal oil. For example, if the amount of riboflavin formation in the culture medium without blended with clay mineral is regarded to be 100%, then, the amount of riboflavin formation increases to 159% (about 1.6 times) when the culture medium is blended with 1% by weight of sepiolite even when other conditions remain the same (for the details of experiment, refer to Example 1).

In the fermentation of riboflavin, the plant oil or the animal oil which is an organic matter is decomposed by the riboflavin-producing microbes to accumulate the riboflavin which is a metabolized product. According to the study conducted by the present inventors, it was learned that a process leading to the decomposition includes a process in which the plant oil or the animal oil is, first, taken in by the microbes, and a process in which the plant oil or the animal oil taken in by the microbes is decomposed.

Figure 1:
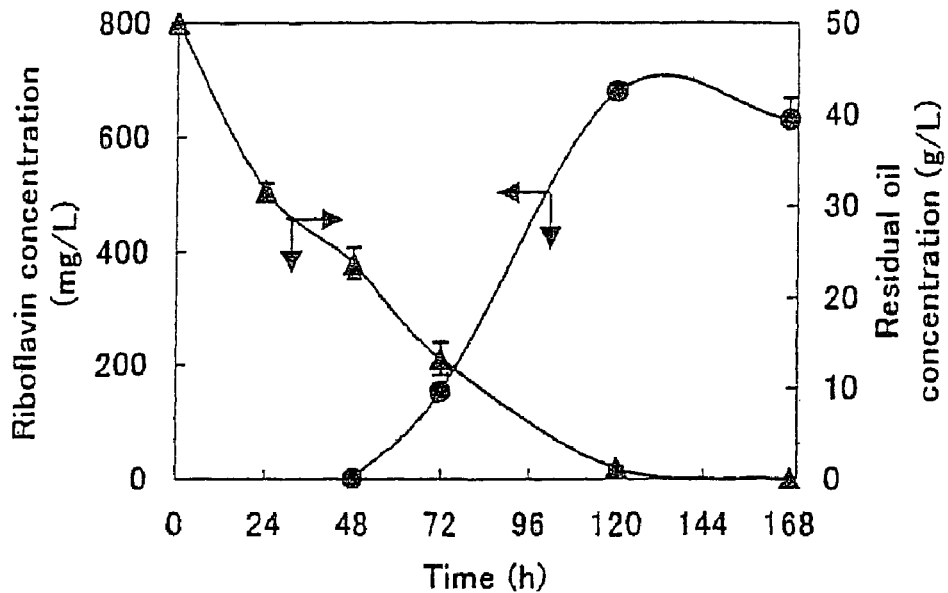
FIG. 1 is a graph plotting relationships among the culturing time, residual amount of oil and amount of riboflavin that is formed by making a plant oil of soybean present in 50 cc of a culture medium (indicating the commencement of riboflavin formation 48 hours after the start)
Figure 2:
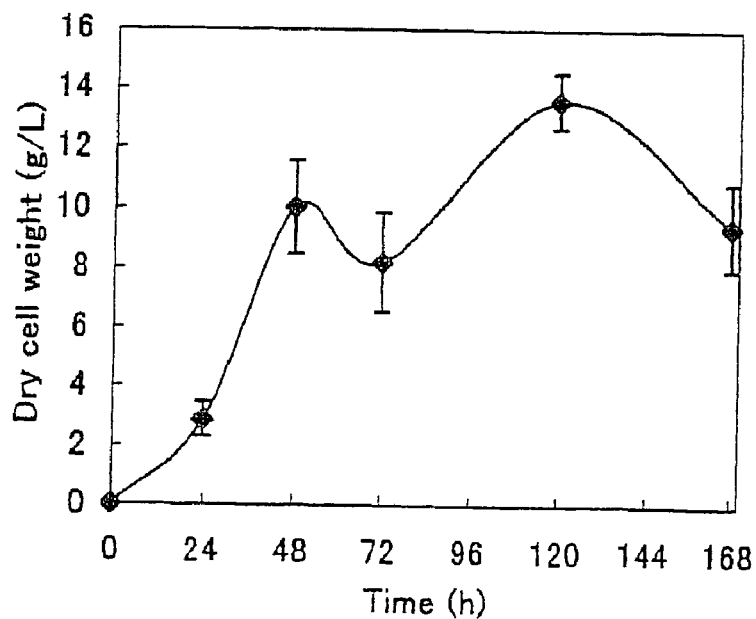
FIG. 2 is a graph plotting a relationship between the culturing time and an increase in the weight of microbes.

FIG. 1 in the accompanying drawings is a graph plotting relationships among the culturing time, residual amount of oil and amount of riboflavin that is formed by making a plant oil of soybean present in 50 cc of a culture medium, and FIG. 2 is a graph plotting a relationship between the culturing time and an increase in the weight of microbes.

According to FIG. 1, the amount of oil in the culture medium is monotonously decreasing with the passage of the culturing time. Here, there exists a predetermined time lag between the reduction in the amount of oil in the culture medium and the amount of riboflavin formation. In the concrete example shown here, the formation of riboflavin commences after 48 hours have passed from the start.

Figure 3:
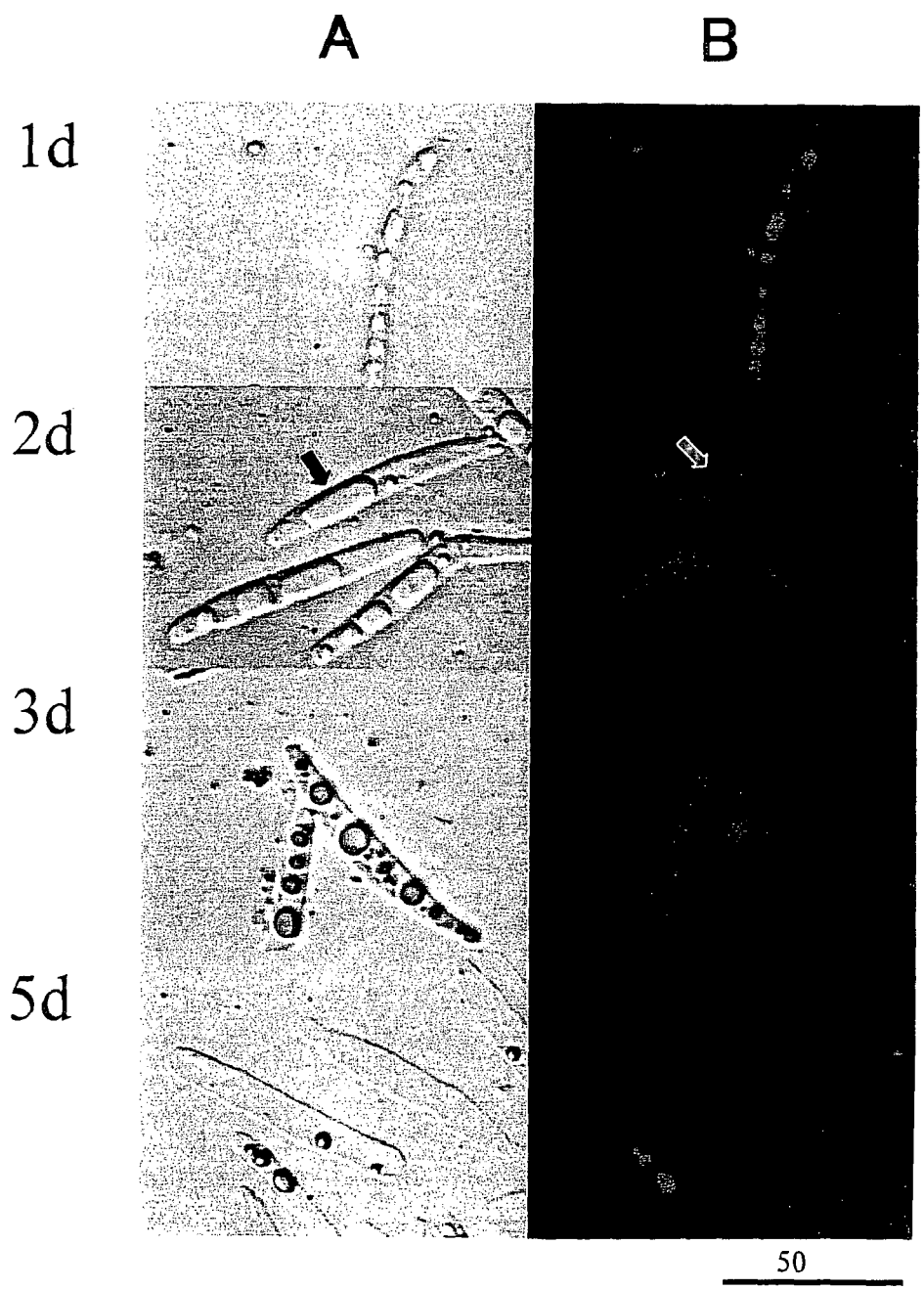
FIG. 3 shows a microphotograph (A)(×600 times) of microbes after 48 hours have passed and a fluorescent microphotograph (B)(×600 times) of microbes by dying the oil component of microbes with Nile red.

FIG. 3 in the accompanying drawings shows a microphotograph (A)(×600 times) of microbes after 48 hours have passed and a microphotograph (B)(×600 times) of when the oil component of microbes is dyed with Nile red and when the dyed microbes are observed by using a fluorescent microscope. In FIG. 3(B), a portion indicated by a white arrow is an oil component that is dyed. Referring to these photographs, the plant oil in the culture medium is, first, taken in by the microbes and is, then, decomposed to accumulate the riboflavin which is a metabolized product.

The clay mineral having oil-adsorbing property or the chemically treated product thereof used in the present invention promotes the microbes to take in the plant oil or the animal oil in the culture ground and, further, enhances the yield of riboflavin formation.

Figure 4:
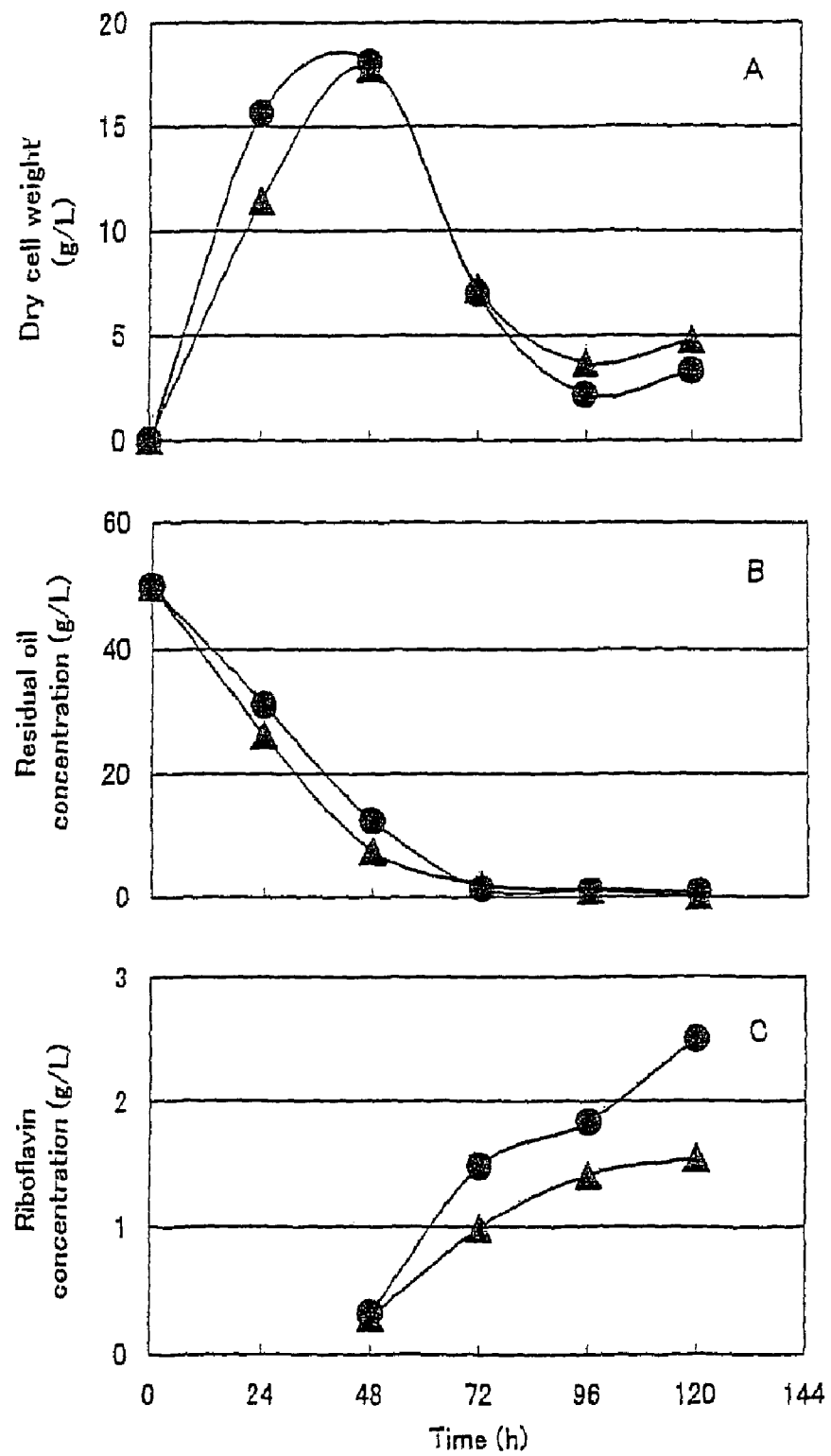
FIG. 4 is a graph plotting relationships (A) between the culturing time and the increase in the weight of microbes, relationships (B) between the culturing time and the residual oil concentration, and relationships (C) between the culturing time and the riboflavin concentration when a sepiolite is added in an amount of 1% to the culture medium (•) and when it is not added (▲) while stirring the culture medium at a speed of 600 rpm.

FIG. 4 in the accompanying drawing is a graph plotting relationships (A) between the culturing time and the increase in the weight of microbes, relationships (B) between the culturing time and the residual oil concentration, and relationships (C) between the culturing time and the riboflavin concentration when a sepiolite is added in an amount of 1% to the culture medium (•) and when it is not added (▲) while stirring the culture medium at a speed of 600 rpm.

The results tell that when the sepiolite is added, the formation of riboflavin is promoted though the absorption of oil is nearly the same.

The carrier of the clay mineral having oil-absorbing property, the chemically treated product thereof or the calcium compound used for the present invention, exists stably in an aqueous phase which is the culture medium like the riboflavin-producing microbes, takes in the oil component due to its oil-adsorbing property, disperses it in water in the form of fine particles, makes it easy to take in the oil components by the microbes, and promotes these actions.

These are the actions and advantages obtained by the addition of the clay mineral or the chemically treated product thereof as the carrier.

The clay mineral or the chemically treated product thereof and the plant oil or the animal oil can be made present in the culture medium by employing a variety of means or measures. For example, the clay mineral or the chemically treated product thereof and the plant oil or the animal oil can be independently added to the culture medium or can be added to the culture medium in the form of compositions.

In one aspect of the invention, the carrier of the clay mineral or the like is made present in the culture medium in a state of occluding the plant oil or the animal oil. The waste clay is the easiest form of obtaining the carrier occluding the plant-oil or the animal oil.

The acid clay or the activated clay obtained by chemically treating the acid clay is widely used for decoloring and refining fats and oils. In carrying out this processing, however, there is produced waste clay arousing a problem concerning the disposal thereof. That is, the waste clay contains oils in amounts of from about 20 to about 60% by weight. Besides, the waste clay is in the form of a sticky paste which is very difficult to handle. The waste clay is produced in amounts of as large as 50,000 tons a year. According to the present invention, however, the waste clay is utilized as a carrier occluding the plant oil or the animal oil for the fermentation of riboflavin. Namely, the plant oil or the animal oil in the waste clay is effectively used as a resource making it further possible to reuse the clay from which the plant oil or the animal oil has been removed. Effective reuse of the resource makes it possible to effectively prevent the contamination of natural environment.

The fermentation of riboflavin according to the present invention exhibits a very favorable advantage in that the riboflavin that is formed is adsorbed by the clay mineral or the like which is the carrier. Namely, in an ordinary fermentation method, a considerable amount of energy cost is required for the concentration since the formed riboflavin has been contained in a dilute state in the culture ground.

According to the fermentation method of the present invention, on the other hand, the formed riboflavin is existing being adsorbed by the clay mineral or the like which is the carrier. Therefore, the carrier adsorbing the riboflavin may be separated from the culture medium, and the riboflavin may be extracted from the carrier that is separated, requiring a simple operation for effecting the concentration and saving the costs that may be involved.

The present invention further favorably makes use of the oil component extracted from the waste clay occluding the plant oil or the animal oil as the carbon source, offering an advantage from the standpoint of effectively utilizing the waste clay.

When the calcium carbonate which is the representative example of the calcium compound is used as the carrier, further, the calcium carbonate prevents a drop in the pH value that is caused by fatty acid formed by the decomposition of oils and fats, preventing the microbes from being damaged and maintaining a high yield of riboflavin formation (see Example 13). As will be understood from Comparative Example 8, further, when the magnesium hydroxide which is a magnesium compound is used as an alkaline earth metal which is the same as calcium, there is no problem from the standpoint of proliferating the microbes without, however, increasing the production of riboflavin. This is attributed to that the fatty acid formed by the decomposition of oils and fats is not used for the production of riboflavin but is used as a source of energy for proliferating the microbes and is, then, used for promoting the formation of spores when there is no carbon source.

[Clay Minerals and their Chemically Treated Products]

The clay mineral or the chemically treated product thereof used as a carrier in the present invention has oil-absorbing property and, generally, has fibrous, scale-like or laminar appearance, and finely disperses in either the water phase or the oil phase.

As a preferred example of oil-adsorbing clay mineral, there can be exemplified a chained clay mineral.

The chained clay minerals used in the present invention are fibrous magnesium silicate clay minerals as represented by sepiolite, attapulgite and palygorskite. They have three-dimensional chained structure. Unlike the two-dimensional crystalline structure such as talc, they are the porous clay minerals having large specific surface areas with holes formed in the gaps of the chained structure in a range of from 100 to 350 m²/g as measured by the BET specific surface area method and having adsorbing action.

Unlike the ordinary laminar clay mineral as represented montmorillonite which is also a porous clay mineral, the sepiolite has a distinguished feature in that it does not swell in an aqueous system.

Due to the features possessed by the chained clay mineral such as sepiolite, i.e., due to the fibrous state and porous property, the chained clay mineral entangles well with the microbes to firmly and stably secure the microbes, rendering the secured microbes to be porous, enabling the culture solution and oxygen to be favorably supplied to the microbes and improving filtering property.

In the present invention, the above chained clay mineral can be used in a single kind, as well as in combination with a fibrous mineral of a two-layer structure such as halloysite or asbestos or in combination with volcanic fibrous mineral including Kanuma earth or Akadama earth. As required, further, the fibrous clay mineral may be used in combination with an adsorptive clay mineral as represented by zeolite or acid clay or with rocks such as cristobalite, quartz or feldspar.

The sepiolite preferably used in the present invention has a chemical structure as represented by the formula (1),

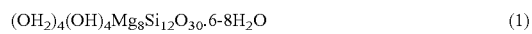

$$(OH_2)_4(OH)_4Mg_8Si_{12}O_{30} \cdot 6\text{-}8H_2O \quad (1)$$

and in which the two-dimensional crystalline structure such as of talc has a chained crystalline structure like that of when bricks are alternately stacked.

Further, though it has a fibrous structure due to holes formed by the chained gaps, the sepiolite has distinguished features, i.e., a large specific surface area and a large adsorbing property different from those of other fibrous minerals.

The present invention preferably uses the sepiolite having a specific surface area in a range of from 100 to 350 m²/g, and absorbing oils in an amount of from 100 to 300 ml/100 g. When the surface area is smaller than this range, the oil-adsorbing property is not enough. Even when the specific surface area is larger than this range, on the other hand, the effect does not increase correspondingly.

Further, the fibrous sepiolite preferably used in the present invention, usually, has a fiber diameter of 70 to 400 angstroms, a fiber length of 0.2 to 400 μm and an aspect ratio of from 5 to 500.

The following Table 1 shows a general chemical composition of sepiolite (dried at 110° C. for two hours).

TABLE 1

| General chemical composition of sepiolite. | |
|---|---|
| SiO₂ | 52.50 |
| | (% by weight) |
| MgO | 22.8 |
| Al₂O₃ | 1.7 |
| Fe₂CO₃ | 0.8 |
| CaO | 0.8 |
| H₂O⁺ | 10.5 |
| H₂O⁻ | 11.0 |

In the present invention, smectite clay minerals such as acid clay (montmorillonite), bentonite, saponite, hectorite and stevensite as well as acid-treated products thereof, can be used as carriers.

Among these clay minerals, the clay minerals of montmorillonite and the acid-treated products thereof are suited for the object of the present invention. They are widely used for decoloring and refining oils and fats.

The montmorillonite clay mineral such as the acid clay is an aluminosilicate having, as a basic unit, a three-layer structure in which an $AlO_6$ octahedral layer is sandwiched between the two $SiO_4$ tetrahedral layers, the three-layer structures of this basic unit being further laminated in many number in the C-axis direction to constitute a laminar crystalline structure. This laminar crystalline structure is common in the clay minerals of montmorillonite.

Among the montmorillonites, the acid clay widely produced in Japan are weathered and Al atoms in the $AlO_6$ octahedral layer in the three-layer structure which is the basic unit of the montmorillonite are partly substituted by an alkaline earth metal such as magnesium or calcium, and hydrogen ions are bonded thereto to compensate for an atomic value. Therefore, if the acid clay is suspended in an aqueous solution of table salt to measure its pH value, the acidic property is exhibited since the hydrogen ions are replaced by the sodium (Na) ions. On the other hand, the bentonite exhibits a pH which is neutral to very weakly alkaline since the exchangeable cations are mostly those of sodium (Na) and further exhibits a large water-swelling property. On the other hand, the acid clay is very advantageous from the standpoint of adsorption since the sodium ions have been substituted by an alkaline earth metal, the amount of the alkali metal component is small, the water-swelling property is small, and the silicic acid is contained in large amounts. As the montmorillonite, therefore, any acid clay produced in Japan is widely used. There is further used a clay mineral of montmorillonite called sub-bentonite (Ca-type bentonite).

The following Table 2 shows a general chemical composition of acid clay (dried at 100° C.).

TABLE 2

| | |
|---|---|
| $SiO_2$ | 61.0 to 74.0 (% by weight) |
| $Al_2O_3$ | 12.0 to 23.0 |
| $Fe_2O_3$ | 2.0 to 3.5 |
| MgO | 3.0 to 7.0 |
| CaO | 1.0 to 4.0 |
| $K_2O$ | 0.3 to 2.0 |
| $Na_2O$ | 0.3 to 2.0 |
| Ig. loss | 5.0 to 10.0 |

In using the acid clay, the rocks such as cristobalite, quartz and feldspar contained therein can be easily separated by a separation method utilizing the difference in the specific gravity (such classification means as hydraulic elutriation, air elutriation, etc.). Among them, the cristobalite of crystalline silicic acid easily reacts with an alkali and can be converted into an alkali silicate, and can, hence, be removed even by this method.

On the other hand, the acid-treated product of acid clay has been known as activated clay which can be used as an agent for refining oils and fats. The acid-treated product can be easily prepared by treating the acid clay with a mineral acid solution such as of sulfuric acid or hydrochloric acid, partly eluting the basic component contained therein and washing it. Due to this treatment with acid, the laminar crystalline structure possessed by the acid clay is partly destroyed, but the content of silicic acid ($SiO_2$) increases contributing to increasing the specific surface area and improving properties such as adsorption properties. The acid-treated product of acid clay and, generally, activated clay that is generally placed in the market and production intermediate products thereof, serve as refining agents exhibiting excellent properties.

The acid-treated product usually possesses the composition shown in Table 3 below though it may vary depending upon the kind of the starting acid clay or the conditions for the treatment with acid.

TABLE 3

| | |
|---|---|
| $SiO_2$ | 65.0 to 83.0 (% by weight) |
| $Al_2O_3$ | 5.0 to 12.0 |
| $Fe_2O_3$ | 1.0 to 3.5 |
| MgO | 1.0 to 7.0 |

TABLE 3-continued

| | |
|---|---|
| CaO | 0.5 to 4.0 |
| $K_2O$ | 0.2 to 2.0 |
| $Na_2O$ | 0.2 to 2.0 |
| Ig. loss | 5.0 to 10.0 |

It is desired that the acid clay and the activated clay are used in the invention in the form of a so-called waste clay occluding plant oils or animal oils.

[Calcium Compounds]

Concrete examples of the calcium compound that can be used as a carrier include natural calcium carbonate (bathylite, calcite, aragonite), synthetic calcium carbonate, calcium silicate, calcium hydroxide, calcium phosphate (apatite, etc.). Particularly preferably, calcium carbonate is used.

[Other Carriers]

As the carriers, there can be used natural silica, synthetic silica, hollow silica, diatomaceous earth, perlite, magnesium carbonate, magnesium silicate, magnesium ferrosilicate, brucite, and synthetic magnesium hydroxide in combination with the above-mentioned carriers.

[Plant Oils and Animal Oils]

The plant oil used as a carbon source in the present invention exists widely in the natural plant world and chiefly comprises an ester of fatty acid and glycerin. Examples include safflower oil, soybean oil, rape oil, palm oil, palm kernel oil, cotton seed oil, coconut oil, rice bran oil, sesame oil, castor oil, linseed oil, olive oil, tung oil, tsubaki oil, peanut oil, kapok oil, cacao oil, Japan wax, sunflower oil and corn oil. It is desired that the plant oil used in the present invention at least partly comprises chiefly an ester of an unsaturated fatty acid and glycerin. As the animal oil, there can be used fish oils such as sardine oil, herring oil cuttlefish oil, saury oil, as well as lever oil, whale oil, beef tallow, buttermilk, lard, chicken oil, horse oil, and sheep oil.

[Waste Clays]

The waste clay used in the method of the present invention is separated as a by-product in the step of decoloring or refining oils and fats by using the clay for decoloring or refining. The waste clay used in the present invention contains oil components and it is not allowed to discard it from the standpoint contaminating the environment. It has therefore been eagerly desired to effectively utilize the waste clay.

That is, to the oils and fats that are to be decolored or refined, there is added a clay mineral of montmorillonite such as acid clay or activated clay that is obtained by treating the above clay mineral with an acid and/or an alkali in the form of a powdery agent for decoloring or refining, so that the two are homogeneously stirred together and that the color components and impurity components contained in the oils and fats are adsorbed in the clay particles. The clay separated after the decoloring or refining contains oil components in an amount of from about 20 to about 60% by weight.

The oils and fats are decolored under known conditions by, for example, adding 0.1 to 5% of clay as a decoloring or refining agent based on the weight of the oils and fats, and stirring the two compositions at a temperature of from 90 to 150° C. for 5 to 30 minutes to thereby complete the processing for decoloring or refining.

The mixture after decolored or refined is supplied to any filter such as a filter press, a belt filter, the Oliver filter, the American filter or to a pressure-reducing or a pressurizing filter such as a centrifugal filter, to obtain refined oils and fats and the so-called waste clay which is the used decoloring or refining agent. The waste clay usually contains from about 20 to about 60% by weight of oil components held by the particles though it may vary depending upon the kind of the starting oil that is to be refined. It is further considered that the waste clay has a catalytic function.

In the present invention, the waste clay can be used as a carbon source for fermenting the riboflavin.

[Riboflavin-Producing Microbes]

In the present invention, any known microbes that have been known to produce riboflavin can be used as riboflavin-producing microbes.

As the riboflavin-producing microbes, there can be used *Eremothecium ashbyii, Ashbya gossypii, Candida flareri, Mycocandida riboflavina, Clostridium acetobutylicum, Bacillus* riboflavin-producing microbes, variable strains of *streptomyces testaceus, Acromobacter* riboflavin-producing microbes, *Previbacterium* riboflavin-producing microbes, *Saccharomyces* riboflavin-producing microbes, *Candida phamata* (ATCC20849), etc.

Among these riboflavin-producing microbes, it is desired to use those that are capable of taking in the plant oil or the animal oil as a carbon source. A preferred example is *Ashbya gossypii* ATCC10895.

[Culture Grounds]

The fermentation method of the invention uses a plant oil or an animal oil as a carbon source in the culture medium. It is of course allowable to use, in combination, a carbon source of other than the plant oil or the animal oil. As the carbon sources that can be used in combination, there can be exemplified saccharides such as glucose, galactose, maltose, cellobiose, arabinose and sucrose, sugaralcohols such as glycerin, organic acids such as acetic acid, gluconic acid, succinic acid, formic acid, citric acid, fumaric acid, glutamic acid, lactic acid and salts thereof, and alcohols such as methanol and ethanol.

As the nitrogen source in the culture medium, there can be used organic or inorganic ammonium compounds such as ammonia, ammonia chloride, ammonia sulfate, ammonia carbonate, ammonia phosphate and ammonia acetate, urea or derivatives thereof as well as any other natural nitrogen sources.

As the organic material, there can be used salts of metals such as sodium, potassium, magnesium, calcium, zinc, cobalt, nickel, copper and manganese, as well as salts of hydrochloric acid, sulfuric acid, phosphoric acid or nitric acid, in one kind or in a combination of plural kinds.

When the microbes that are used requests nutrient, the required substance is added to the culture medium. As required, further, natural nutrients, hydrolyzed products of various microorganisms, yeast extract, sake lees extract, meat extract, peptone, and decomposed soybean cakes can be added to the culture medium.

Depending upon the cases, there can be further added a variety of substances such as purines as represented by guanine, adenine and hypoxanthine, pyrimidines as represented by thymine, urasine and cytosine, as well as saccharides thereof or derivatives of phosphonated saccharide to increase the amount of formation of riboflavin.

In the present invention, the riboflavin can be cultured under known conditions. The culturing conditions such as temperature and the like lie under the known ranges and are, usually, from 20 to 35° C. and, particularly, from 25 to 30° C.

There exist optimum ranges even in the aqueous phase and the oil phase in the culture medium. The aqueous phase and the oil phase exist at a weight ratio of, generally, in a range of from 200:1 to 3:1 and, particularly, from 50:1 to 10:1.

When the amount of oil phase is greater than the above range or is smaller than the above range, the rate of forming the riboflavin tends to decrease.

In the present invention, there also exists an optimum range in the amount of the carrier in the culture ground. It is desired that the amount of the carrier is from 0.1 to 10% by weight per the culture medium and, particularly, from 0.5 to 5% by weight.

When the amount of the carrier is too small, the productivity of riboflavin decreases and when the amount of the carrier is too great, growth of the riboflavin is hindered causing a drop in the production of the riboflavin.

When the waste clay containing oil components is used as the starting material and as the carrier according to a preferred embodiment of the present invention, it is desired that the waste clay contains the aqueous phase and the oil components at a weight ratio of from 100:1 to 5:1 and, particularly, from 20:1 to 5:1.

The rate of forming the riboflavin tends to decrease when the amount of the waste clay phase is either greater than the above range or smaller than the above range.

The emulsifying method of the present invention needs not remain adamant on the above-mentioned order of adding the above three components, and there can be selected a method of adding the carrier to the water, stirring the mixture, adding the oil thereto and stirring and emulsifying the mixture, though it may vary depending upon the ratio of blending the oil phase and the aqueous phase, or the use thereof, conditions of use and the kind of the oil. More preferably, however, the carrier is added to the oil and is stirred and, then, water is added, and the mixture is stirred and emulsified to obtain a more stable emulsified composition. It is desired that the stirring is effected at a speed of 400 to 700 rpm.

The emulsifying operation according to the invention may be a generally employed physical method such as stirring. On a laboratory scale, the emulsifying operation may be accomplished based on a mechanical force having a shearing force which is nearly equal to that of ordinary household mixer, which is continued for several tends of seconds to several minutes. For carrying out the processing in large amounts on an industrial scale, there can be exemplified a homogenizer, a colloidal mill, a jet flow mixer or a votator. The invention, however, is in no way limited to the above physical methods only but, as required, there can be employed a chemical method such as an inverted emulsifying method, a gel emulsifying method or an HLB-temperature emulsifying method.

To culture the microbes, the emulsifying agent comprising the clay mineral of the invention is added to the culture medium containing the useful microbes and oils and fats. Then, by using an ordinary aerated stirrer vessel or a reactor such as a filled bed-type reactor or an air-lift type air bubble tower, the emulsified composition formed as described above is cultured by any one of a batchwise system, a half-batchwise system, a recurring batchwise system or a continuous system depending upon the properties of the fermented product.

EXAMPLES

The invention will now be described by way of the Examples to which only, however, the invention is in no way limited.

(Measuring Methods)

(1) Measuring the Amount of Oil Consumption.

5 Milliliters of hexane was added to 5 ml of a culture solution and was mixed together for two minutes. The mixture was subjected to the centrifugal separation at 3000 rpm for 15 minutes. The hexane layer was removed, dried at 105° C. for 3 hours to find the residual amount of oil which was, then, subtracted from the amount of oil initially used to find the amount of consumption.

(2) Measuring the Riboflavin Concentration.

The culture solution was so diluted that the riboflavin concentration was not higher than 30 mg/L, and 0.2 ml of 1N NaOH was mixed into 0.8 ml of the diluted culture solution. The culture solution to which NaOH has been mixed was picked up in an amount of 0.4 ml, and to which was further added 1 ml of a 0.1M phosphoric acid buffer solution (pH 6.0). The mixture was subjected to the centrifugal separation at 11,000 rpm for 10 minutes, and the supernatant solution was taken out and was measured for its absorbency at a wavelength of 444 nm. The riboflavin concentration was calculated in a unit of mg/L according to absorbency×times of dilution×127.2971 at the wavelength of 444 nm.

(3) Absorbancy.

Measured by using a model U-2001 manufactured by Hitachi, Ltd.

(4) Fluorescent Microphotograph.

Observed by using a model IX-70 manufactured by Olympus Kogaku Kogyo Co.

Example 1

Cultured in a Flask (Pre-Culture)

30 Grams of a CSL (corn steep liquor), 9 g of an yeast extract and 15 g of a soybean oil were dissolved together, and to which was added distilled water such that the volume was one liter. Then, 5N KOH was added thereto to adjust the pH to be 6.8 thereby to prepare a culture medium.

100 Milliliters of the thus prepared culture medium was introduced into a 500-ml flask and was sterilized. Then, *Ashbya gossypii* ATCC 10895 was implanted and was cultured at 28° C., 220 rpm for 24 hours to obtain a pre-cultured solution.

(Main Culture)

50 Grams of a soybean oil and 11.1 g of sepiolite (trade name: Aidplus ML-50D, manufactured by Mizusawa Kagaku Co.) were mixed together. This mixture as well as 30 g of gelatin, 60 g of CSL, 1.5 g of $KH_2PO_4$, 1.5 g of glycine, 2 mg of $Co^{2+}$, 5 mg of $Mn^{2+}$, 10 mg of $Zn^{2+}$ and 1 mg of $Mg^{2+}$ were dissolved in one liter of distilled water, and the pH was adjusted with 5N KOH to be 6.8 to prepare a culture medium. The sepiolite concentration in the culture medium was 1.1% by weight (in Examples appearing later, the sepiolite was the above one manufactured by Mizusawa Kagaku Co.).

50 Milliliters of the above culture medium was introduced into a 500-ml flask and was sterilized. Then, 1 ml of the pre-cultured solution was implanted and was cultured at 28° C., 220 rpm for 7 days. The obtained riboflavin concentration, yield (%) and increment (%) were as shown in Table 4.

The increment was found in accordance with the following formula, $$\text{Increment}(\%) = (A-B) \times 100/B$$

wherein A is a riboflavin concentration of when the sepiolite is added, and B is a riboflavin concentration of when no sepiolite is added.

The yield was represented by the amount (%) of riboflavin produced from one gram of the starting oil (soybean oil in this case).

Examples 2 to 4

Culture media for the main culture were prepared by adjusting the pH to 6.8 in the same manner as in Example 1 with the exception of changing the amount of the sepiolite to 22.3 g, 33.4 g and 55.7 g. The sepiolite concentrations in the obtained culture media were 2% by weight, 3% by weight and 5% by weight, respectively.

50 Milliliters of the above culture medium was introduced into the 500-ml flask and was sterilized. Then, 1 ml of the pre-cultured solution prepared in Example 1 was implanted and was cultured at 28° C., 220 rpm for 7 days. The obtained riboflavin concentrations, yields (%) and increments (%) were as shown in Table 4.

Comparative Example 1

A culture medium for the main culture having a pH adjusted to 6.8 was prepared in the same manner as in Example 1 but without using sepiolite.

50 Milliliters of the above culture medium was introduced into the 500-ml flask and was sterilized. Then, 1 ml of the pre-cultured solution prepared in Example 1 was implanted and was cultured at 28° C., 220 rpm for 7 days. The obtained riboflavin concentration, yield (%) and increment (%) were as shown in Table 4.

TABLE 4

|  | Ex. 1 | Ex. 2 | Ex. 3 | Ex. 4 | Comp. Ex. 1 |
| --- | --- | --- | --- | --- | --- |
| Amount of sepiolite | 1 wt % | 2 wt % | 3 wt % | 5 wt % | 0 wt % |
| Riboflavin concentration | 1,100 mg/L | 1,001 mg/L | 966 mg/L | 863 mg/L | 690 mg/L |
| Yield (%) | 2.2 | 2.0 | 1.9 | 1.7 | 1.4 |
| Increment | 59% | 45% | 40% | 25% | 0% |

Examples 5 to 7

Jar Fermentator Culture (Pre-Culture)

2 Grams of an yeast extract, 20 g of a peptone, 0.6 g of a myoinositol and 10 g of a glucose were dissolved in one liter of distilled water, and the pH was adjusted to 6.8 with 5N KOH to obtain a culture medium A.

Further, 30 g of a CSL (corn steep liquor), 9 g of an yeast extract and 15 g of a soybean oil were dissolved together, and to which was added distilled water such that the volume was one liter. Then, 5N KOH was added thereto to adjust the pH to be 6.8 thereby to prepare a culture medium B.

50 Milligrams of the culture medium A was introduced into a 500-ml Erlenmeyer flask and was sterilized. Then, *Ashbya gossypii* ATCC 10895 was implanted and was pre-cultured at 28° C., 220 rpm for 24 hours to obtain a culture solution A.

Next, 100 ml of the culture medium B was introduced into the 500-ml Erlenmeyer flask and was sterilized. Then, 1 ml of the culture solution A obtained above was implanted and was put to the secondary culture for 24 hours to obtain a secondary culture solution.

(Main Culture)

A culture medium for main culture (sepiolite concentration of 1% by weight) was prepared in quite the same manner as in Example 1. Two liters of this culture medium was introduced into a 5-liter jar fermentator and was sterilized. Then, 100 ml of the secondary culture solution obtained above was implanted and cultured for 5 days. Oxygen (1 vvm) was supplied while changing the stirring speed to 400 to 700 rpm.

Table 5 shows the concentrations of the obtained riboflavin and increments (%). The results of Table 5 are those obtained by conducting the experiments twice at different stirring speeds.

Comparative Examples 2 to 4

A culture medium for main culture without containing sepiolite was prepared in quite the same manner as in Comparative Example 1. Two liters of this culture medium was introduced into a 5-liter jar fermentator and was sterilized. Then, 100 ml of the secondary culture solution prepared in Example 5 was implanted and cultured for 5 days. Oxygen was supplied while changing the stirring speed to 400 to 700 rpm.

Table 5 shows the concentrations of the obtained riboflavin and increments (%).

TABLE 5

| | Stirring speed | Riboflavin concentration | Increment |
|---|---|---|---|
| Example 5-1 | 400 rpm | 1,230 mg/L | 583% |
| Comp. Ex. 2-1 | 400 rpm | 180 mg/L | — |
| Example 5-2 | 400 rpm | 1,094 mg/L | 501% |
| Comp. Ex. 2-2 | 400 rpm | 182 mg/L | — |
| Example 6-1 | 600 rpm | 2,380 mg/L | 54% |
| Comp. Ex. 3-1 | 600 rpm | 1,550 mg/L | — |
| Example 6-2 | 600 rpm | 2,500 mg/L | 44% |
| Comp. Ex. 3-2 | 600 rpm | 1,731 mg/L | — |
| Example 7-1 | 700 rpm | 1,922 mg/L | 27% |
| Comp. Ex. 4-1 | 700 rpm | 1,515 mg/L | — |
| Example 7-2 | 700 rpm | 1,580 mg/L | 35% |
| Comp. Ex. 4-2 | 700 rpm | 1,169 mg/L | — |

Example 8

The strain *Ashbya gossypii* ATCC 10895 was proliferated on a solid culture medium (pH 6) containing 10 g of an yeast extract, 10 g of a glucose, 3 g of a glycine and 20 g/L of an agar-agar at 30° C. for two days (solid culture).

Next, a culture medium of distilled water containing 30 g/L of a CSL, 15 g/L of an yeast extract and 6 g/L of a soybean oil was sterilized, and to which was implanted a loopful of the above solid culture to conduct the pre-culture at 28° C., 220 rpm for 24 hours to obtain a pre-cultured solution.

Next, 30 g of a gelatin, 60 g of a CSL, 1.5 g of $KH_2PO_4$, 1.5 g of a glycine, 2 mg of $Co^{2+}$, 5 mg of $Mn^{2+}$, 10 mg of $Zn^{2+}$, 1 mg of $Mg^{2+}$ and a carbon source were dissolved in one liter of distilled water, and the pH was adjusted to 6.8 with 5N KOH to prepare a culture medium for the main culture. As the carbon source, there was used 125 g of waste clay containing 40% by weight of rape oil.

2 Milliliters of the pre-culture solution was implanted onto the thus prepared culture medium for main culture, and was cultured in a rotary shaker at 200 rpm, 28° C. for 7 days.

After the culture has been finished, the waste clay was separated, and 1.5 g of its wet weight (weight of 0.636 g after dried at 105° C. for 2 hours) was taken out to extract the riboflavin. The method of extraction consisted of adding 0.4 N NaOH to the waste clay followed by vigorous stirring to measure the concentration of the supernatant riboflavin.

As a result, the riboflavin could be recovered by more than 80% through two times of extraction, and could be recovered by more than 90% through three times of extraction. Table 6 shows the obtained riboflavin concentrations and yields (%).

Example 9

By using the strain *Ashbya gossypii* ATCC 10895, a pre-culture solution was obtained by conducting the solid culture and the pre-culture in the same manner as in Example 8.

Further, the main culture was conducted in quite the same manner as in Example 8 but by using 125 g of waste clay containing 40% by weight of palm oil as a carbon source, and the riboflavin was extracted in the same manner as in Example 8. Table 6 shows the obtained riboflavin concentration and the yield (%).

Examples 10 and 11

By using the strain *Ashbya gossypii* ATCC 10895, a pre-culture solution was obtained by conducting the solid culture and the pre-culture in the same manner as in Example 8.

The main culture was conducted in quite the same manner as in Example 8 but by using, as a carbon source, 50 g of the rape oil or the palm oil extracted from the waste clay.

After the culture has been finished, the concentration of oil and the concentration of riboflavin were measured, and the yields (%) were calculated from the measured results.

To calculate the concentration of oil, 2 ml of the culture solution after the culture has been finished was picked up, the same amount of hexane was added thereto and was mixed well for 2 minutes. The mixture was then put to the centrifugal separation at 3000 rpm, the supernatant solution was taken out, and hexane was vaporized, followed by drying. Then, the weight of oil was measured to calculate the concentration of oil. The concentration of the riboflavin was calculated according to the above-mentioned method.

Table 6 shows the riboflavin concentrations and the yields (%).

TABLE 6

|  | Ex. 8 | Ex. 9 | Ex. 10 | Ex. 11 |
| --- | --- | --- | --- | --- |
| Kind of oil | rape oil | palm oil | ext. oil 1 | ext. oil 2 |
| Riboflavin concentration | 1,123.2 | 880.0 | 833.4 | 863.9 |
| Yield (%) | 2.2 | 2.2 | 1.7 | 1.7 |

Ext. oil 1: Rape oil extracted from the waste clay.
Ext. oil 2: Palm oil extracted from the waste clay.
Riboflavin concentration: in a unit of mg/L Comparative Examples 5 and 6

By using the strain *Ashbya gossypii* ATCC 10895, pre-cultured solutions were obtained by conducting the solid culture and the pre-culture in the same manner as in Example 8.

Further, the main culture was conducted in quite the same manner as in Example 8 but by using 50 g of the virgin soybean oil (reagent manufactured by Wako Junyaku Co.) or the rape oil (reagent manufactured by Nakaraitesk) as a carbon source.

After the culture has been finished, the concentration of oil and the concentration of riboflavin were measured in the same manner as in Examples 10 and 11, and the yields (%) were calculated from the measured results. Table 7 shows the obtained riboflavin concentrations and the yields (%)

TABLE 7

|  | Comp. Ex. 5 | Comp. Ex. 6 |
| --- | --- | --- |
| Kind of oil (virgin oil) | soybean oil | rape oil |
| Riboflavin concentration (mg/L) | 768.2 | 778.6 |
| Yield (%) | 1.5 | 1.6 |

Example 12

By using the strain *Ashbya gossypii* ATCC 10895, a pre-cultured solution was obtained by conducting the solid culture and the pre-culture in the same manner as in Example 8.

Further, the main culture was conducted in quite the same manner as in Example 8 but by using 188 g of waste clay containing 40% by weight of palm oil as a carbon source and conducting the main culture for 10 days, and the riboflavin was extracted in the same manner as in Example 8. Table 8 shows the obtained riboflavin concentrations and the yields (%).

Comparative Example 7

By using the strain *Ashbya gossypii* ATCC 10895, a pre-cultured solution was obtained by conducting the solid culture and the pre-culture in the same manner as in Example 8.

Further, the main culture was conducted in quite the same manner as in Example 12 but by using 75 g of the virgin palm oil (Spectrum Chemical Mfg. Corp.) as a carbon source.

After the culture has been finished, the concentration of oil and the concentration of riboflavin were measured in the same manner as in Examples 10 and 11, and the yields (%) were calculated from the measured results. Table 8 shows the obtained riboflavin concentrations and the yields (%).

TABLE 8

|  | Example 12 | Comp. Ex. 7 |
| --- | --- | --- |
| Kind of oil | palm oil | palm oil (virgin) |
| Riboflavin concentration (mg/L) | 2500 | 1600 |
| Yield (%) | 3.8 | 2.5 |

Example 13

A calcium carbonate adsorbing 50 g of a rape oil (PC manufactured by Shiroishi Calcium Kogyo Co.) was prepared in an amount of 125 g. This calcium carbonate as well as 30 g of a gelatin, 60 g of CSL, 1.5 g of $KH_2PO_4$, 1.5 g of a glycine, 2 mg of $Co^{2+}$, 5 mg of $Mn^{2+}$, 10 mg of Zn and 1 mg of $Mg^{2+}$ were dissolved in one liter of distilled water, and the pH was adjusted with 5N KOH to be 6.8 to prepare a culture medium for the main culture. 50 Milliliters of the above culture medium was introduced into a 500-ml flask and was sterilized. Then, 1 ml of the pre-cultured solution prepared in Example 1 was implanted and was cultured at 28° C., 220 rpm for 7 days. The obtained riboflavin concentration and the yield (%) were as shown in Table 9.

Comparative Example 8

The main culture was conducted in the same manner as in Example 13 but using 125 g of magnesium hydroxide adsorbing 50 g of the rape oil instead of using the above calcium carbonate. The obtained riboflavin concentration and the yield (%) were as shown in Table 9.

Comparative Example 9

The main culture was conducted in the same manner as in Example 13 but using 125 g of silica (MIZUCASIL P707 manufactured by Mizusawa Kogaku Kogyo Co.) adsorbing 50 g of the rape oil instead of using the above calcium carbonate. The obtained riboflavin concentration and the yield (%) were as shown in Table 9.

TABLE 9

|  | Example 13 | Comp. Ex. 8 | Comp. Ex. 9 |
| --- | --- | --- | --- |
| Kind of carrier | Ca carbonate | Mg hydroxide | silica |
| Riboflavin concentration (mg/L) | 1200 | 0 | 390 |
| Yield (%) | 2.4 | 0 | 0.7 |

Example 14

By using the strain *Ashbya gossypii* ATCC 10895, a pre-cultured solution was obtained by conducting the solid culture and the pre-culture in the same manner as in Example 8.

Further, the main culture was conducted in quite the same manner as in Example 8 but by using 125 g of waste clay containing 40% by weight of beef tallow and lard (a mixture of beef tallow:lard=1:1) as a carbon source, and the riboflavin was extracted in the same manner as in Example 8. Table 10 shows the obtained riboflavin concentrations and the yields (%).

Comparative Example 10

By using the strain *Ashbya gossypii* ATCC 10895, a pre-cultured solution was obtained by conducting the solid culture and the pre-culture in the same manner as in Example 8.

Further, the main culture was conducted in quite the same manner as in Example 14 but by using 50 g of the virgin beef tallow as a carbon source. Table 10 shows the obtained riboflavin concentration and the yield (%).

Comparative Example 11

By using the strain *Ashbya gossypii* ATCC 10895, a pre-cultured solution was obtained by conducting the solid culture and the pre-culture in the same manner as in Example 8.

Further, the main culture was conducted in quite the same manner as in Comparative Example 10 but by using 50 g of the virgin beef tallow as a carbon source. Table 10 shows the obtained riboflavin concentration and the yield (%).

TABLE 10

|  | Example 14 | Comp. Ex. 10 | Comp. Ex. 11 |
| --- | --- | --- | --- |
| Kind of animal oil and fat | beef tallow, lard | beef tallow | lard |
| Riboflavin concentration (mg/L) | 997.16 | 335.64 | 260.53 |
| Yield (%) | 1.99 | 0.67 | 0.52 |

According to the method of producing riboflavin by culturing riboflavin-producing microbes in a culture medium by using a plant oil or an animal oil as a carbon source, forming and accumulating the riboflavin therein and collecting the riboflavin, a carrier of a clay mineral having oil-adsorbing property, a chemically treated product thereof or a calcium compound is made present in the culture medium making it possible to stably disperse the plant oil in the culture medium without effecting the stirring operation to such an excess degree as to damage the microbes and, hence, to produce the riboflavin in high yields and at high production rates.

The invention further provides a method of producing riboflavin by culturing riboflavin-producing microbes in a culture medium by using a plant oil or an animal oil as a carbon source, wherein the plant oil or the animal oil is dispersed in the culture medium in an improved manner, so that riboflavin can be produced in high yields and at high production rates.

The invention further provides a method of producing riboflavin at a low cost without requiring cumbersome operations such as condensing or recovering the riboflavin.

The invention further makes it possible to effectively recover the riboflavin from the waste plant oil or the waste animal oil that is to be disposed of. The recovered riboflavin can be used as a medicine, an additive for animal feeds, a food coloring agent and a nutrition aid. When carried by the clay mineral, further, the riboflavin can be favorably used as animal feeds to supplement nutrition and for enhancing intestinal action. In particular, the waste clay is effectively utilized and, at the same time, the environmental burden can be decreased. It is also allowable to add the carrier used in the invention to the waste edible oils discharged from the domestic use, quick snack shops, bakeries, etc. which are casting problems from the standpoint of disposal, in order to produce the riboflavin therefrom.

The invention claimed is:

1. A method of producing riboflavin comprising culturing riboflavin-producing microbes in a culture medium containing a waste clay obtained from a process of decoloring or refining oils and fats wherein said waste clay contains oils and fats adsorbed in said process, and forming and accumulating riboflavin therein and collecting riboflavin therefrom, wherein said oils and fats adsorbed by said waste clay comprise a carbon source for said microbes, said waste clay being obtained as a by-product of decoloring or refining oils and fats, said waste clay containing oil components in an amount of from about 20 to about 60% by weight adsorbed therein at the time of decoloring or refining.

* * * * *